(12) United States Patent
Schmidt et al.

(10) Patent No.: US 8,524,261 B2
(45) Date of Patent: Sep. 3, 2013

(54) PIGMENTS

(75) Inventors: Christoph Schmidt, Kriftel (DE); Sabine Schoen, Herten (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 12/911,885

(22) Filed: Oct. 26, 2010

(65) Prior Publication Data

US 2011/0104220 A1 May 5, 2011

(30) Foreign Application Priority Data

Oct. 29, 2009 (DE) .......................... 10 2009 051 171

(51) Int. Cl.
*A61K 8/02* (2006.01)
*A61K 8/27* (2006.01)
*A61K 8/28* (2006.01)
*A61K 8/29* (2006.01)
*C04B 14/34* (2006.01)
*C04B 14/04* (2006.01)

(52) U.S. Cl.
USPC ........... 424/401; 106/425; 106/450; 106/459; 106/426; 106/457; 424/69; 424/63

(58) Field of Classification Search
None
See application file for complete search history.

(56) References Cited

U.S. PATENT DOCUMENTS

| 6,117,435 A | 9/2000 | Painter et al. | |
|---|---|---|---|
| 6,648,958 B2 * | 11/2003 | Anselmann et al. | 106/442 |
| 2008/0181920 A1 * | 7/2008 | Buerger et al. | 424/401 |
| 2008/0181921 A1 * | 7/2008 | DeLuca | 424/401 |
| 2008/0279796 A1 * | 11/2008 | Handrosch et al. | 424/63 |
| 2009/0142382 A1 * | 6/2009 | Shah et al. | 424/401 |

FOREIGN PATENT DOCUMENTS

WO    WO 99/66883    12/1999

* cited by examiner

*Primary Examiner* — Robert A Wax
*Assistant Examiner* — Danah Al-Awadi
(74) *Attorney, Agent, or Firm* — Millen, White, Zelano & Branigan, P.C.

(57) ABSTRACT

The present invention relates to inorganic spherical pigments which are based on spherical particles having a particle diameter of 0.1-100 μm and are coated on the surface with agglomerates selected from the group $ZrO_2$, ZnO, $Al_2O_3$, $TiO_2$, $Fe_2O_3$, $Fe_3O_4$, FeOOH and $BaSO_4$ or mixtures thereof, and are optionally coated with a further layer (2nd layer) comprising a metal oxide, lake or Berlin Blue, and to the use thereof in paints, coatings, printing inks, security printing inks, plastics, ceramic materials, glasses, in cosmetic formulations, as tracer, as filler and for the preparation of pigment preparations and dry preparations.

16 Claims, No Drawings

PIGMENTS

The present invention relates to inorganic pigments based on spherical particles, where the spherical particles have a diameter of <100 μm and are coated on the surface (1st layer) with agglomerates selected from the group $ZrO_2$, ZnO, $Al_2O_3$, $TiO_2$, $Fe_2O_3$, FeOOH and $BaSO_4$ or mixtures thereof, and to the use thereof in paints, coatings, printing inks, security printing inks, plastics, ceramic materials, glasses, as tracer and in particular in cosmetic formulations.

The term pigments is applied to colorants which are insoluble in the application medium. Typical examples of organic pigments are phthalocyanines, diketopyrrolopyrroles, azo pigments and quinacridones. Inorganic pigments which may be mentioned are the various types of iron oxides or also ultramarine. Pigments are generally distinguished compared with dyes, which are soluble in the application medium, by higher chemical and photochemical stability.

Fillers can be regarded as a special form of pigments. In fillers, it is not the "colouring" function that is in the foreground. Instead, factors such as an increase in mechanical stability, abrasion resistance, weather stability or also production costs are crucial for use of industrial fillers.

Fillers are also widely used in cosmetic formulations. For example, powders may comprise up to 50% of fillers, based on the final formulation. Typical values are 10-15% of fillers in lipsticks and 2-6% of fillers in emulsions. Cosmetic fillers have a wide variety of functions: in foundations, they prevent an undesired greasy sheen on the skin due to the so-called matting effect, while in powders they help, for example, to improve the pouring behaviour or the skin application properties. In deodorant products, the high liquid-absorption capacity is utilized by some fillers.

Before use in the system to be pigmented, fillers or pigments in cosmetics have to be converted into a form which enables easy dispersal and a reproducible colour. This pretreatment of the pigments, for example grinding, which crucially influences the quality of the end product, is time-consuming and expensive. A further disadvantage is that the colour of the pigment is modified on wetting. For cosmetic formulations, the pigments must additionally have a good skin feel, which the classical fillers only exhibit to a small extent.

Fillers based on spherical particles, in particular $SiO_2$ spheres, are increasingly employed in cosmetics since on the one hand they impart a natural appearance on the human skin and on the other hand can make wrinkles less visible.

Inorganic spherical fillers which are coated with a colouring layer are known, for example, from the published specifications JP 62-288662, JP 11-139926, JP 11-335240 and DE 199 29 109.

WO 00/15720 discloses a pigment mixture based on spherical $SiO_2$ particles having high light diffusion, where some of the $SiO_2$ spheres are coated with $TiO_2/SiO_2$ and the remainder are coated with $TiO_2$ and $Fe_2O_3$.

WO 99/66883 describes $SiO_2$ spheres coated with metal oxides, such as titanium, iron or zinc oxide, which have a final $SiO_2$ layer. The $SiO_2$ spheres coated in this way are employed in cosmetic formulations as a mixture with interference pigments.

The fillers based on $SiO_2$ spheres which are known from the prior art exhibit a relatively good skin feel, but have the disadvantage of having an excessively high scattering capacity. The reason for this lies in the structure of the metal-oxide layers of the spherical fillers. The functional pigments from the prior art generally consist of very small particles, i.e. they have particle sizes of 0.5-100 nm, which cover the surface of the carrier spheres in a uniform arrangement. Light is reflected at the layer surface, causing lustre. At the same time, however, a considerable amount of scattering takes place, since individual particles, which act as strong scattering centres, form on the layer. As a consequence of these two contradictory effects (lustre and scattering), the pigments have a white and unnatural appearance on the skin.

The object of the present invention is therefore to provide a functional pigment which, besides a good skin feel, at the same time has good dispersibility in cosmetic formulations, chemical and photochemical stability and a pure colour. In addition, the pigment should exhibit a soft and even and natural appearance on the skin when applied to the skin as a pure powder, in creams, emulsions, foundations and the like. It is furthermore desired for the pigment to provide, in particular, liquid and pasty preparations with a slight increase in solidity. This significantly improves the application behaviour of the preparation. The viscosity should be optimised by the pigment in the manner desired for the particular application. A slightly thixotropic function of the pigment significantly simplifies distribution of the cosmetic preparations on the skin. Thus, it is possible to prepare high-viscosity creams, i.e. solid foundations, which nevertheless have very good spreadability on the skin and/or have very good removal behaviour on removal from the container.

Besides these product properties, a further object of the invention is simple industrial preparation of the pigment.

A further object is to enable the adjustment of certain properties, such as, for example, the hiding power and colour intensity, of the pigment to be monitored in a simple manner in the course of the preparation process.

Surprisingly, it has been found that pigments based on spherical particles having a diameter of 0.1-100 μm which are coated on the surface (1st layer) with agglomerates selected from the group $ZrO_2$, ZnO, $Al_2O_3$, $TiO_2$, $Fe_2O_3$, $Fe_3O_4$, FeOOH and $BaSO_4$ or mixtures thereof allow better adjustment of the hiding power and a significantly more natural appearance of the skin and in addition have a better skin feel than the fillers/pigments from the prior art. In addition, the pigments according to the invention exhibit the desired influence on the texture, i.e. they slightly increase the viscosity of emulsions and the solidity of foundations without adversely affecting the application properties.

The invention therefore relates to pigments which are distinguished by the fact that they are based on spherical particles having a particle diameter of 0.1-100 μm and are coated on the surface with agglomerates selected from the group $ZrO_2$, ZnO, $Al_2O_3$, $TiO_2$, $Fe_2O_3$, $Fe_3O_4$, FeOOH and $BaSO_4$ or mixtures thereof, and are optionally coated with a further layer (2nd layer) comprising a metal oxide or metal-oxide mixture, a lake or Berlin Blue.

Compared with the known pigments, the spherical pigments according to the invention exhibit
  a more natural appearance of the skin
  easier dispersibility
  improved processability
  a hiding power which can be adjusted within broad limits
  an improved skin feel
  an improved texture of the cosmetic preparations
  improved application behaviour of the cosmetic formulations
  greater whiteness
  higher colour purity.

The invention furthermore relates to the use of the spherical pigments according to the invention in paints, coatings, preferably in industrial coatings, printing inks, security printing inks, plastics, ceramic materials, glasses, as tracer, as filler and in particular in cosmetic formulations. The pigments according to the invention are furthermore also suitable for the preparation of pigment preparations and for the preparation of dry preparations, such as, for example, granules, chips, pellets, sausages, briquettes, etc. The dry preparations are used, in particular, in printing inks and in cosmetics.

Suitable base substrates are spherical particles, as, for example, are commercially available, inter glia from Sunjin Chemical, Omega Materials, 3M, Dow Corning or Evonik. Preferred spherical particles are selected from the group magnesium silicate, aluminium silicate, alkali-metal aluminium silicates, alkaline-earth metal aluminium silicates and combinations thereof, silicon dioxide, glass spheres, hollow glass spheres, nylon, polyacrylates and aluminium oxide.

Particularly preferred spherical substrates are magnesium silicates and alkali-metal aluminium silicates, as marketed, for example, by 3M under the trade names Ceramic Microspheres and Cosmetic Microspheres or Zeeospheres.

Substrates which can be used are also mixtures of different substrates. It is preferred to use not more than two different substrates. Particularly preferred substrate mixtures are:
  alkali-metal aluminium silicate and magnesium silicate
  alkali-metal aluminium silicate and silicon dioxide
  alkali-metal aluminium silicate and alkaline-earth metal aluminium silicate.

The microscale spherical base substrates of the pigments according to the invention have a particle diameter of 0.1-100 µm, preferably 0.3-50 µm, in particular 0.5-15 µm.

The microscale spherical base particles are coated on the surface (1st layer) with agglomerates, which preferably comprise at least one metal oxide, in particular from the group $ZrO_2$, $ZnO$, $Al_2O_3$, $TiO_2$, $Fe_2O_3$, $Fe_3O_4$, $FeOOH$ or mixtures thereof. The agglomerate may furthermore also consist of $BaSO_4$ or a mixture of $BaSO_4$ and one or more of the said metal oxides.

The base particles preferably have a coating of agglomerates comprising $TiO_2$. The $TiO_2$ here can be in the rutile or anatase modification, preferably in the anatase form.

Coating(s) in this patent application are taken to mean the partial or complete covering of the base particles with metal oxides and/or with $BaSO_4$, where both the metal oxide(s) or the $BaSO_4$ are in the form of agglomerates.

Agglomerates in this application are taken to mean oxide or $BaSO_4$ particles distributed irregularly on the surface of the spherical base particles. The formation of agglomerates reduces the number of light-scattering centres, and the scattering capacity of the coating increases less with increasing coverage than in the case of coating with non-aggregated individual particles. The partial vertical arrangement of a plurality of oxide particles to give agglomerates also results in an irregular layer thickness of the coating and in a fissured surface. The interaction with the medium is therefore more intense, and networks are able to form between the coated spherical particles, causing a desired increase in viscosity and an improvement in the solidity of a foundation and at the same time improving the application behaviour.

The average layer thickness of the first layer comprising the spherical particles is preferably 0.01-2 µm, in particular 0.02-1 µm, very particularly preferably 0.05-0.8 µm.

Since the agglomerates are distributed very irregularly on the surface, the average layer thickness of the agglomerates, i.e. the layer thickness for an assumed uniform and compact (non-agglomerated) distribution of the layer material on the substrate surface, is indicated in this application.

In order to improve the dispersibility, the chemical and photochemical stability and the skin feel, it is frequently advisable to apply a top layer (final layer) comprising $SiO_2$.

The $SiO_2$ layer generally has an average layer thickness of 0.01-1 µm, in particular 0.02-0.7 µm and very particularly preferably 0.05-0.5 µm.

This final $SiO_2$ layer sheathes the agglomerate-coated spherical particles in a thin layer. It improves the dispersibility and prevents chemical and photo-chemical interactions of the pigment according to the invention with the application medium.

The spherical base particles are preferably coated with one or two layers. Particular preference is given to the coating of the spherical base particles with a colourless first layer, such as, for example, $TiO_2$, or the setting of the mass tone by means of a mixture of $TiO_2/Fe_2O_3$ and optionally by means of a top layer of $SiO_2$.

A second coating comprising a metal oxide, preferably $Fe_2O_3$ or $Fe_3O_4$, a lake or Berlin Blue can optionally also be applied to the first coating. The second coating can also be a metal-oxide mixture consisting of two, three or more metal oxides. The metal-oxide mixture preferably consists of two metal oxides, in particular of $TiO_2$ and $Fe_2O_3$.

Lakes are organic colorants which are bonded to an inorganic support matrix. Suitable as support matrix are, in particular, network-forming inorganic oxides, such as, for example, $Al_2O_3$ and $SiO_2$. Organic colorants which may be mentioned are all coloured compounds which can be converted into lakes, in particular the alkali and alkaline-earth metal salts of Carmine Red (CAS No. 1390-65-4), Allura Red (CAS No. 25956-17-6), tartrazine (CAS No. 1934-21-0), Brilliant Blue FCF (CAS No. 3844-45-9), erythrosine (CAS No. 16423-68-0) and Phloxine B (CAS No. 18472-87-2). This list only represents a small number of the possible lakes and should not be understood as being restrictive.

Berlin Blue is the iron(III) salt of the hexacyanoferrate(II) anion, having the empirical formula $Fe_4[Fe(CN)_6]_3$. It can easily be prepared by combining the solutions of potassium hexacyanoferrate(II) and iron(III) salts or potassium hexacyanoferrate(III) and iron(II) salts in weakly acidic solution.

The average layer thicknesses of the second layer comprising metal oxide, lake or Berlin Blue are 10-500 nm, preferably 10-200 nm and particularly preferably 10-100 nm. The proportion by weight of the lake in the pigment as a whole is dependent on the desired colour intensity of the product and the colouring effect of the respective lake. It is 0.1-30%, preferably 0.2-25% and particularly preferably 0.5-20%.

Particularly preferred pigments according to the invention have the following coating on the surface:
spherical base substrate+$TiO_2$
spherical base substrate+$TiO_2$+$SiO_2$
spherical base substrate+$TiO_2/Fe_2O_3$
spherical base substrate+$TiO_2/Fe_2O_3$+$SiO_2$
spherical base substrate+$Fe_2O_3$+$SiO_2$
spherical base substrate+$FeO(OH)$+$SiO_2$
spherical base substrate+$Fe_3O_4$+$SiO_2$
spherical base substrate+$TiFe_2O_5$+$SiO_2$
spherical base substrate+$TiO_2$+$Fe_2O_3$+$SiO_2$
spherical base substrate+$TiO_2$+$Fe_3O_4$+$SiO_2$
spherical base substrate+$TiO_2$+$Fe_4[Fe(CN)_6]_3$
spherical base substrate+$TiO_2$+$Fe_4[Fe(CN)_6]_3$+$SiO_2$
spherical base substrate+$TiO_2$+carmine lake
spherical base substrate+$TiO_2$+carmine lake+$SiO_2$.

Particular preference is given to pigments which are based on Al or Mg silicate spheres and have a coating of a metal oxide, preferably $TiO_2$ or $Fe_2O_3$, and optionally a top layer (final layer) comprising $SiO_2$.

The final $SiO_2$ layer in the case of the pigments according to the invention enables the optical properties of the pigments in colour, colour purity and colour strength, and the applicational properties, such as, for example, dispersibility, skin feel and chemical and photochemical stability, to be improved.

The spherical pigments according to the invention generally have an oil absorption value of 10-200, in particular 20-200, very particularly preferably 50-150. The oil absorption value in this patent application is determined in accordance with DIN ISO 787/5-1980 (E).

The BET surface area of the pigments according to the invention, determined by nitrogen absorption, is generally 1-200 m$^2$/g, preferably 2-150 m$^2$/g, in particular 3-100 m$^2$/g. The BET surface area in this patent application is determined in accordance with DIN ISO 9277: 2003-05.

The pigments according to the invention improve, in particular, the texture of cosmetics by achieving easier application and more uniform distribution on the skin and improving the skin feel. Since the pigments are built up on a mineral basis and comprise predominantly inorganic components, they are very well tolerated by the skin.

The preparation of spherical particles is known. Thus, for example, Mg or Al silicate spheres are generally melted by heating the finely divided silicate raw materials and/or oxidic starting compounds thereof in a gas stream and thus adopt a spherical shape. In order to make the melting easier by lowering the melting point, finely divided alkali and/or alkaline-earth metal compounds are typically added to the reaction mixture.

The coating of the spherical base particles can be carried out in a one-pot process. The pigments according to the invention can be prepared relatively simply in various ways. The spherical particles can be coated with one or more coatings by wet-chemical coating or by the CVD or PVD process.

The coating of the spherical base particles is preferably carried out in the wet-chemical method by hydrolytic deposition or the metal oxides or metal hydroxides from salt solutions thereof. The formation of agglomerates can be caused by a suitable choice of the precipitation conditions. These are, in particular, the reaction temperature, the pH, the stirring speed and the metering rate of the salt solutions. TiO$_2$ precipitations are typically carried out in the pH range from 1.0 to 3.0. The tendency towards agglomerate formation increases from pH 1.0 to pH 3.0. However, if an excessively high pH is selected, so-called secondary precipitation may occur, i.e. the TiO$_2$ particles precipitate alongside the base particles and do not form a layer. For the said base particles, different precipitation conditions, which can easily be determined by the person skilled in the art in the area of pigments, should generally be selected owing to the different surface behaviour.

The invention also relates to a process for the preparation of the pigments according to the invention, in which the spherical particles are coated with the agglomerates by precipitation of the layer material in aqueous suspension by substantially uniform and simultaneous or non-simultaneous addition of the solutions of the agglomerate- or layer-forming raw materials in the presence of acids or bases, filtered off, washed, dried, optionally calcined and sieved.

The metal-oxide layers on the spherical particles are preferably applied by wet-chemical methods, where in general the wet-chemical coating methods developed for the preparation of pearlescent pigments can be used. Methods of this type are described, for example, in U.S. Pat. Nos. 3,087,828, 3,087,829, 3,553,001, DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017, DE 196 18 568, EP 0 659 843, or also in further patent documents and other publications known to the person skilled in the art.

In the case of wet-chemical coating, the spherical particles are suspended in water, and one or more hydrolysable metal salts are added at a pH which is suitable for hydrolysis, which is selected so that the metal oxides or metal oxide hydrates are precipitated directly onto the spheres as agglomerates. The pH is usually kept constant by simultaneous metered addition of a base or acid. The pigments are subsequently separated off, washed and dried, preferably at 50-350° C., in particular at 80-150° C., and optionally calcined, where the calcination temperature can be optimised with respect to the coating present in each case. In general, the calcination temperatures are between 250 and 1100° C., preferably between 350 and 900° C. If desired, the pigments can be separated off after application of individual coatings, washed and optionally calcined and then re-suspended again for the precipitation of the further layers.

The coating can furthermore also be carried out by gas-phase coating in a fluidised-bed reactor, where, for example, the processes proposed in EP 0 045 851 and EP 0 106 235 for the preparation of pearlescent pigments can be used correspondingly. In the case where the colouring layers comprise Fe$_3$O$_4$ or other reduced oxide types, a reduction step, for example calcination in a reducing atmosphere, may be necessary as the final process step.

For the application of a final SiO$_2$ layer, the process described in DE 196 18 569 is preferably used. For the production of the SiO$_2$ layer, sodium or potassium water-glass solution is preferably employed.

In the case of barium sulfate precipitation, solutions of a barium salt, for example barium chloride, and of a sulfate, for example sodium sulfate, are metered in simultaneously. In both processes, oxide or sulfate nuclei form in the solution and precipitate on the surface of the spherical particles as agglomerates.

When the desired amount of the layer material has precipitated, the reaction is interrupted and a pH which is suitable for work-up, for example pH 5, is set.

For work-up, the coated spherical particles are filtered off, washed with water and preferably dried at temperatures of 50-350° C. for a period of 1-20 h and optionally calcined at temperatures of 350-1100° C. for 0.1-2 h. Finally, the pigment is sieved.

The hue and hiding power of the pigments according to the invention can be varied within broad limits through the choice of the coating materials and the coverage rates or the layer thicknesses resulting therefrom. Fine tuning for a certain hue can be achieved, beyond the pure choice of amounts, by approaching the desired colour under visual or measurement-technology control.

In the case of coating with lakes, a matrix of silicon dioxide, aluminium oxide or a mixture of the two is generally applied first. This is carried out, for example, by the process described in DE 2429762 and EP 1595921 by hydrolysis of silicate or aluminate solutions. In a second step, the organic component of the lake in dissolved form is adsorbed onto the matrix in the presence of suitable cations of, for example, calcium, aluminium or barium, as described, for example, in EP 1595921.

in the case of Berlin Blue, solutions of potassium hexacyanoferrate(II) and an iron(II) sulfate solution are added to the aqueous pigment suspension in the presence of an oxidant. On use of iron(III) solution, for example iron(III) chloride, the addition of an oxidant is unnecessary. As an alternative to potassium hexacyanoferrate(II), it is also possible to employ potassium hexacyanoferrate(III), in which case an iron(II) compound, for example iron(II) sulfate solution, must be added. Corresponding processes for carrying out Berlin Blue precipitations are described, for example, in DE 2313332, EP 1595921, EP 1254928 and EP 0659843.

In order to increase the light, water and weather stability, it is frequently advisable, depending on the area of application, to subject the finished pigment or finished filler to post-coating or post-treatment. Suitable post-coating or post-treatment methods are, for example, those described in German Patent 22 15 191, DE-A 31 51 354, DE-A 32 35 017 or DE-A 33 34 598. This post-coating on the final $SiO_2$ layer further increases the chemical and photochemical stability or makes handling of the absorption pigment, in particular incorporation into various media, easier. In order to improve the wettability, dispersibility and/or compatibility with the application media, functional coatings comprising $Al_2O_3$ or $ZrO_2$ or mixtures thereof can be applied to the pigment surface. Furthermore, organic post-coatings are possible, for example with silanes, as described, for example, in EP 0090259, EP 0 634 459, WO 99/57204, WO 96/32446, WO 99/57204, U.S. Pat. No. 5,759,255, U.S. Pat. No. 5,571,851, WO 01/92425 or in J. J. Ponjeé, Philips Technical Review, Vol. 44, No. 3, 81 ff. and P. H. Harding J. C. Berg, J. Adhesion Sci. Technol. Vol. 11 No. 4, pp. 471-493.

The pigments according to the invention are compatible with a multiplicity of colour systems, preferably from the area of paints, coatings and printing inks. A multiplicity of binders, in particular water-soluble products, as marketed, for example, by BASF, Marabu, Pröll, Sericol, Hartmann, Gebr. Schmidt, Sicpa, Aarberg, Siegberg, GSB-Wahl, Follmann, Ruco or Coates Screen INKS GmbH, are suitable for the preparation of printing inks for, for example, gravure printing, flexographic printing, offset printing or offset overprint varnishing. The printing inks can be water-based or solvent-based. Furthermore, the pigments are also suitable for the laser marking of paper and plastics, and for applications in the agricultural sector, for example for greenhouse sheeting, and, for example, for the colouring of tarpaulins.

The present invention allows the preparation of pigments of particularly high colour purity and extraordinarily high hiding power. Particularly effective effects can therefore be achieved with the pigments according to the invention in the various application media, for example in cosmetic formulations, such as, for example, nail varnishes, lipsticks, compact powders, gels, lotions, soaps, toothpastes, in paints, in industrial coatings and powder coatings, and in plastics and in ceramics.

Owing to the good skin feel and the very good skin adhesion, the pigments according to the invention are particularly suitable as filler in decorative cosmetics, but also for personal care applications, such as, for example, body lotions, emulsions, soaps, shampoos, etc.

The pigments according to the invention have a high specific surface area. They are consequently particularly suitable for use in cosmetics in which liquid-absorbent properties are desired, such as, for example, in deodorants and matting creams.

It goes without saying that the pigments according to the invention can also advantageously be employed for the various applications as a blend with, for example, metal-effect pigments, for example based on iron flakes or aluminium flakes;

pearlescent pigments based on metal oxide-coated synthetic mica flakes, natural mica flakes, glass flakes, $Al_2O_3$ flakes, $Fe_2O_3$ flakes or $SiO_2$ flakes;

interference pigments based on metal oxide-coated synthetic mica flakes, natural mica flakes, glass flakes, $Al_2O_3$ flakes, $Fe_2O_3$ flakes or $SiO_2$ flakes;

goniochromatic pigments;

multilayered pigments (preferably comprising 2, 3, 4, 5 or 7 layers) based on metal oxide-coated synthetic mica flakes, natural mica flakes, glass flakes, $Al_2O_3$ flakes, $Fe_2O_3$ flakes or $SiO_2$ flakes;

organic dyes;

organic pigments;

inorganic pigments, such as, for example, transparent and opaque white, coloured and black pigments;

flake-form iron oxides;

holographic pigments;

LCPs (liquid crystal polymers);

carbon black.

The pigments according to the invention can be mixed in any ratio with commercially available pigments and/or further commercially available fillers.

Commercially available fillers which may be mentioned are, for example, natural and synthetic mica, nylon powder, pure or filled melanine resins, talc, glasses, kaolin, oxides or hydroxides of aluminium, magnesium, calcium, zinc, BiOCl, barium sulfate, calcium sulfate, calcium carbonate, magnesium carbonate, carbon, boron nitride and physical or chemical combinations of these substances. There are no restrictions with respect to the particle shape of the filler. It can be, for example, flake-shaped, spherical or needle-shaped, in accordance with requirements.

The pigments according to the invention can of course also be combined in the formulations with any type of cosmetic raw materials and assistants. These include, inter alia, oils, fats, waxes, film formers, preservatives and assistants which generally determine applicational properties, such as, for example, thickeners and rheological additives, such as, for example, bentonites, hectorites, silicon dioxides, Ca silicates, gelatins, high-molecular-weight carbohydrates and/or surface-active assistants, etc.

The formulations comprising the pigments according to the invention can belong to the lipophilic, hydrophilic or hydrophobic type. In the case of heterogeneous formulations having discrete aqueous and non-aqueous phases, the pigments according to the invention may be present in in each case only one of the two phases or alternatively distributed over both phases.

The pH values of the formulations can be between 1 and 14, preferably between 2 and 11 and particularly preferably between 5 and 8.

No limits are set for the concentrations of the pigments according to the invention in the formulation. They can be—depending on the application—between 0.001 (rinse-off products, for example shower gels) and 60%. The pigments according to the invention may furthermore also be combined with cosmetic active compounds. Suitable active compounds are, for example, insect repellents, UV A/BC protection filters (for example OMC, B3, MBC), anti-ageing active compounds, vitamins and derivatives thereof (for example vitamin A, C, E, etc.), self-tanning agents (for example DHA, erythrulose, inter alia) and further cosmetic active compounds, such as, for example, bisabolol, LPO, ectoin, emblica, allantion, bioflavonoids and derivatives thereof.

The present invention likewise relates to formulations, in particular cosmetic formulations, which, besides the pigment according to the invention, comprises at least one constituent selected from the group of the absorbents, astringents, antimicrobial substances, antioxidants, antiperspirants, antifoaming agents, antidandruff active compounds, antistatics, binders, biological additives, bleaches, chelating agents, deodorisers, emollients, emulsifiers, emulsion stabilisers, dyes, humectants, film-formers, fillers, fragrances, flavours, insect repellents, preservatives, anticorrosion agents, cosmetic oils, solvents, oxidants, vegetable constituents, buffer substances, reducing agents, surfactants, propellant gases, opacifiers, UV filters and UV absorbers, denaturing agents, viscosity regulators, perfume and vitamins.

The invention also relates to the use of the pigments according to the invention in paints, coatings, printing inks, security printing inks, plastics, ceramic materials, glasses, as tracer, in cosmetic formulations and for the preparation of pigment preparations and dry preparations.

The following examples are intended to explain the invention in greater detail, but without restricting it.

EXAMPLES

Example 1

Ceramic Microspheres Coated with Titanium Dioxide and Silicon Dioxide 250 g of spherical silica-alumina ceramic spheres (Zeeospheres W-210, 1-12 μm; manufacturer 3M) are suspended in 1.8 l of demineralised water and heated to 75° C. with vigorous stirring. An amount of 395 g of $TiCl_4$ solution (30%) is metered into this mixture at pH 2.2 at a rate of 3.3 ml/min, and the pH is kept constant by means of sodium hydroxide solution (32%). The pH is then adjusted to 8.0 using sodium hydroxide solution (32%), and 383 g of sodium water-glass solution (13% of $SiO_2$, Merck KGaA) are metered in at this pH at a rate of 1.7 ml/min. The pH is kept constant by means of hydrochloric acid (18%).

For work-up, the pigment is filtered off, washed with 15 l of demineralised water, dried at 110° C. for 16 hours and sieved through a sieve having a mesh width of 32 μm.

A pure-white powder having a very soft skin feel is obtained which is eminently suitable as filler for cosmetic formulations, for example compact powders, lipsticks and pure-white emulsions and creams.

Example 2

Magnesium Silicate Spheres Coated with Titanium Dioxide and Silicon Dioxide 250 g of spherical magnesium silicate (Cosmetic Microspheres CM-111, 1-12 μm; manufacturer 3M) are suspended in 1.8 l of demineralised water and heated to 75° C. with vigorous stirring. An amount of 395 g of $TiCl_4$ solution (30%) is metered into this mixture at pH 2.2 at a rate of 3.3 ml/min, and the pH is kept constant by means of sodium hydroxide solution (32%). The pH is then adjusted to 8.0 using sodium hydroxide solution (32%), and 383 g of sodium water-glass solution (13% of $SiO_2$, Merck KGaA) are metered in at this pH at a rate of 1.7 ml/min. The pH is kept constant by means of hydrochloric acid (18%).

For work-up, the pigment is filtered off, washed with 15 l of demineralised water, dried at 110° C. for 16 hours and sieved through a sieve having a mesh width of 32 μm.

A white powder having a soft skin feel is obtained which is eminently suitable as filler for cosmetic formulations, for example compact powders and lipsticks.

Example 3

Magnesium Silicate Spheres Coated with Barium Sulfate and Silicon Dioxide 200 g of spherical magnesium silicate (Cosmetic Microspheres CM-111, 1-12 μm; manufacturer 3M) are suspended in 1.8 l of demineralised water and heated to 75° C. with vigorous stirring. 20.9 g of $BaCl_2 \times 2H_2O$ are added to this mixture, which is then stirred for a further 15 minutes. 250 g of a sodium sulfate solution ($w(Na_2SO_4)=10\%$) are subsequently metered in over a period of about 80 min. The pH is then adjusted to 8.0 by means of sodium hydroxide solution (32%), and a solution of 118 ml of sodium water-glass solution (about 27% by weight of $SiO_2$, Merck KGaA) in 159 ml of demineralised water is added at this pH at a rate of 1.7 ml/min. The pH is kept constant by means of hydrochloric acid (18%).

For work-up, the pigment is filtered off, washed with 15 l of demineralised water, dried at 110° C. for 16 hours and sieved through a sieve having a mesh width of 32 μm.

A white powder having a good skin feel is obtained which is eminently suitable as filler for cosmetic formulations, for example compact powders and lipsticks.

Example 4

Ceramic Microspheres Coated with Barium Sulfate and Silicon Dioxide 200 g of microspheres (Zeeospheres W-210, 1-12 μm; manufacturer 3M) are suspended in 1.8 l of demineralised water and heated to 75° C. with vigorous stirring. 10.5 g of $BaCl_2 \times 2H_2O$ are added to this mixture, which is then stirred for a further 15 minutes. 125 g of a sodium sulfate solution ($w(Na_2SO_4)=10\%$) are subsequently metered in over a period of about 40 min. The pH is then adjusted to 8.0 by means of sodium hydroxide solution (32%), and a solution of 118 ml of sodium water-glass solution (about 27% by weight of $SiO_2$, Merck KGaA) in 159 ml of demineralised water is added at this pH at a rate of 17 ml/min. The pH is kept constant by means of hydrochloric acid (18%).

For work-up, the pigment is filtered off, washed with 15 l of demineralised water, dried at 110° C. for 16 hours and sieved through a sieve having a mesh width of 32 μm.

A pure-white powder having a very soft skin feel is obtained which is eminently suitable as filler for cosmetic formulations, for example compact powders, lipsticks and pure-while emulsions and creams.

Example 5

Microspheres Coated with Titanium Dioxide and Carmine Lake and Silicon Dioxide 250 g of spherical silica-alumina ceramic spheres (Zeeospheres W-210, 1-12 μm; manufacturer 3M) are suspended in 1.8 l of demineralised water and heated to 75° C. with vigorous stirring. An amount of 395 g of $TiCl_4$ solution (30%) is metered into this mixture at pH 2.2 at a rate of 3.3 ml/min, and the pH is kept constant by means of sodium hydroxide solution (32%).

After a post-stirring time of 15 min., the pH is adjusted to 7.5 by means of sodium hydroxide solution (32%), and 100 g of sodium water-glass solution (5% of $SiO_2$) are metered in at a rate of 3.3 ml/min. The pH is kept constant by means of hydrochloric acid (10% of HCl), and, when the addition is complete, the mixture is stirred for a further 60 min. The pH is subsequently reduced to 5.4 by means of hydrochloric acid (10% of HCl). A solution of 4.0 g of carmine in 350 ml of sodium hydroxide solution (1.1% of NaOH) and a solution of 14.12 g of $CaCl_2 \times 2H_2O$ and 3.53 g of $AlCl_3 \times 6H_2O$ in 350 ml of demineralised water are metered in simultaneously at this pH at a metering rate of 5.5 ml/min. in each case. During this addition, the pH is kept constant at 5.4 by means of hydrochloric acid (10% of HCl). The pH is then adjusted to 8.0 by means of sodium hydroxide solution (32%), and 383 g of sodium water-glass solution (13% of $SiO_2$, Merck KGaA) are metered in at this pH at a rate of 1.7 ml/min. The pH is kept constant by means of hydrochloric acid (18%).

For work-up, the pigment is filtered off, washed with 15 l of demineralised water, dried at 110° C. for 16 hours and sieved through a sieve having a mesh width of 32 μm.

A carmine-red powder having a very soft skin feel is obtained which is eminently suitable as filler for cosmetic formulations, for example compact powders, lipsticks and emulsions and creams.

Example 6

Microspheres Coated with Titanium Dioxide and Berlin Blue 250 g of spherical silica-alumina ceramic spheres (Zeeospheres W-210, 1-12 μm; manufacturer 3M) are suspended in 1.8 l of demineralised water and heated to 75° C. with vigorous stirring. An amount of 395 g of $TiCl_4$ solution (30%) is metered into this mixture at pH 2.2 at a rate of 3.3 ml/min, and the pH is kept constant by means of sodium hydroxide solution (32%). After a post-stirring time of 15 min., the pH is adjusted to pH 7.0 by means of sodium hydroxide solution. A solution consisting of 2.6 g of $FeSO_4 \times 7H_2O$, 0.06 g of sulfuric acid (about 97%) and 65 g of demineralised water is metered in at this pH over the course of about 45 min. During this addition, the pH is kept constant by means of ammonium hydroxide solution (10%). A solution of 3.64 g of $K_4[Fe(CN)_6] \times 3H_2O$ in 195 g of demineralised water is subsequently metered in over the course of about 70 min., and the mixture is stirred for a further 30 min. Throughout the reaction, air (4-6l/h) is blown into the suspension. When the addition of the reaction solutions is complete, the mixture is stirred for a further 30 min.

The pigment is filtered off with suction in a suction filter, washed with 30 l of demineralised water, dried at 100° C. for 12 h and sieved (mesh width 100 μm).

A blue powder having a very soft skin feel is obtained which is eminently suitable as coloured filler for cosmetic formulations, for example compact powders, lipsticks and emulsions and creams.

USE EXAMPLES

Example A1

Eye Shadow Gel

| Raw material | | INCI | [%] |
|---|---|---|---|
| Phase A | | | |
| Timiron Super Gold | (1) | MICA, CI 77891 (TITANIUM DIOXIDE) | 15.00 |

-continued

| Raw material | | INCI | [%] |
|---|---|---|---|
| Pigment according to Example 1 | | | 7.00 |
| Carbopol Ultrez 21 | (2) | Acrylates/C10-30 Alkyl Acrylate crosspolymer | 0.30 |
| Aloe vera powder regular 200x | (3) | Aloe Barbadensis | 0.05 |
| Citric acid monohydrate | (1) | Citric Acid | 0.00 |
| Water, demineralised | | Aqua (Water) | 55.87 |
| Phase B | | | |
| Triethanolamine 90% Care | (4) | Triethanolamine, Aqua (Water) | 0.78 |
| Germaben II | (5) | Propylene Glycol, Diazolidinyl Urea, Methylparaben, Propylparaben | 1.00 |
| Glycerin, anhydrous | (1) | Glycerin | 2.00 |
| Water, demineralised | | Aqua (Water) | 13.00 |
| Phase C | | | |
| Lubrajel DV | (6) | Propylene Glycol, Polyglycerylmethacrylate | 5.00 |

Preparation: Dissolve the aloe vera powder in the water of phase A, then add all pigments and the remaining ingredients apart from the Carbopol and disperse. Acidify using a few drops of citric acid in order to reduce the viscosity, then scatter in the Carbopol with stirring. When completely dissolved, slowly stir in the pre-dissolved phase B (do not homogenise) and subsequently add phase C. If necessary, adjust the pH to between 7.0-7.5 using citric acid solution.

A water-based eye shadow gel formulation containing aloe vera is obtained (fast-drying and easy to apply using the fingers).

Sources of supply:
(1) Merck KGaA/Rona ®
(2) Noveon
(3) Terry Laboratoires, Inc.
(4) BASF AG
(5) ISP Global Technologies
(6) Guardian

Example A2

Creamy Eye Shadow

| Raw material | | INCI | [%] |
|---|---|---|---|
| Phase A | | | |
| Colorona Light Blue | (1) | MICA, CI 77891 (TITANIUM DIOXIDE) CI 77510 (FERRIC FERROCYANIDE) | 10.00 |
| Pigment according to Example 1 | | | 15.00 |
| Talc | (1) | Talc | 12.00 |
| Phase B | | | |
| Crodamol PMP | (2) | PPG-2Myristyl Ether Propionate | 32.80 |
| Miglyol 812 N | (3) | Caprylic/Capric Triglyceride | 12.00 |
| Syncrowax HGLC | (2) | C18-36 Acid Triglyceride | 10.00 |
| Syncrowax HRC | (2) | Tribehenin | 3.00 |
| Parteck ® LUB STA | (1) | Stearic Acid | 3.00 |
| Antaron V-216 | (4) | PVP/Hexadecene Copolymer | 2.00 |
| Oxynex ® K liquid | (1) | PEG-8, Tocopherol, Ascorbyl Palmitate, Ascorbic Acid, Citric Acid | 0.10 |

| Raw material | | INCI | [%] |
|---|---|---|---|
| Propyl 4-hydroxy-benzoate | (1) | Propylparaben | 0.10 |

Preparation: Heat phase B to about 80° C. until everything has melted and cool to 65° C. with stirring. Then add the ingredients of phase A with stirring, and pour the composition into the packaging provided at 65° C. Allow to cool to room temperature.
Sources of supply:
(1) Merck KGaA/Rona ®
(2) Croda GmbH
(3) Sasol Germany GmbH
(4) ISP Global Technologies

Example A3

Face Powder

| Raw material | | INCI | [%] |
|---|---|---|---|
| Phase A | | | |
| Pigment according to Example 4 | | | 20.00 |
| Unipure Yellow LC 182 | (1) | CI 77492 (Iron Oxides) | 1.20 |
| Unipure Red LC 381 | (1) | CI 77491 (Iron Oxides) | 0.20 |
| Unipure Brown LC 889 | (1) | CI 77491 (Iron Oxides) CI 77499 (Iron Oxides) | 0.30 |
| Magnesium stearate | (2) | Magnesium Stearate | 2.00 |
| Talc | (2) | Talc | 71.90 |
| Phase B | | | |
| RonaCare ® all-rac-alpha-tocopheryl acetate | (2) | Tocopheryl Acetate | 0.30 |
| Perfume oil 200 529 | (3) | Perfume | 0.30 |
| Eutanol G | (4) | Octyldodecanol | 3.70 |
| Propyl 4-hydroxy-benzoate | (2) | Propylparaben | 0.10 |

Preparation: Add the constituents of phase A to the mixer (for example La Moulinette from Moulinex) and mix for 2 × 10 seconds. Transfer the mixture into a beaker, add phase B, and stir in advance using the spatula. Again add the mixture of phase A and phase B to the mixer and process for 3 × 10 seconds to give a homogeneous phase.
The pressing pressure for a powder tray having a diameter of 36 mm is about 25 bar.
Sources of supply:
(1) Les Colorants Wackherr
(2) Merck KGaA/Rona ®
(3) Fragrance Resources
(4) Cognis GmbH

Example A4

Mattifying Foundation

| Raw material | | INCI | [%] |
|---|---|---|---|
| Phase A | | | |
| Water, demineralised | | Aqua (Water) | 57.89 |
| Pigment according to Example 3 | | | 6.00 |
| Glycerin (87% extra pure) | (1) | Glycerin, Aqua (Water) | 5.00 |
| RonaCare ® ectoin | (1) | Ectoin | 0.30 |
| Keltrol CG-SFT | (2) | Xanthan Gum | 0.15 |
| Triethanolamine 90% Care | (3) | Triethanolamine, Aqua (Water) | 0.13 |
| Phase B | | | |
| Kronos 1001 | (4) | CI 77891 (Titanium Dioxide) | 4.92 |
| Unipure Yellow LC 182 | (5) | CI 77492 (Iron Oxides) | 1.60 |
| Unipure Red LC 381 | (5) | CI 77491 (Iron Oxides) | 0.20 |
| Unipure Brown LC 889 | (5) | CI 77491 (Iron Oxides) CI 77499 (Iron Oxides) | 0.20 |
| Unipure Blue LC 686 | (5) | CI 77007 (Ultramarin Blue) | 0.08 |
| Phase C | | | |
| Miglyol 812N | (6) | Caprylic/Capric Triglyceride | 7.00 |
| Eutanol G | (7) | Octyldodecanol | 4.00 |
| Montanov 202 | (8) | Arachidyl Alcohol, Behenyl Alcohol, Arachidylglucoside | 4.00 |
| Avocado oil | (9) | Persea Gratissima (Avocado Oil) | 2.00 |
| Eusolex ® 9020 | (1) | Butyl Methoxydibenzoylmethane | 1.50 |
| Hydrolite-5 | (10) | Pentylene Glycol | 1.20 |
| Bentone gel GTCC V | (11) | Stearalkonium Hectorite, Propylene Carbonate, Caprylic/Capric Triglyceride | 1.00 |
| RonaCare ® all-rac-alpha-tocopheryl acetate | (2) | Tocopherylacetate | 0.50 |
| Phenonip | (12) | Phenoxyethanol, Butylparaben, Ethylparaben, Propylparaben, Methylparaben | 0.40 |
| Oxynex ® K liquid | (1) | PEG-8, Tocopherol, Ascorbyl Palmitate, Ascorbic Acid, Citric Acid | 0.03 |
| Phase D | | | |
| Simulgel EG | (8) | Sodium Acrylate/Sodium Acryloyldimethyltaurate Copolymer, Isohexadecane, Polysorbate 80 | 0.60 |
| Phase E | | | |
| Water, demineralised | | Aqua (Water) | 1.00 |

Preparation: Add the Keltrol slowly to the water of phase A and disperse. Scatter in the remaining constituents of phase A with stirring. Add the constituents of phase B to phase A and homogenise using the Ultra-Turrax T25 (red-blue setting, 13500-20500 rpm) for 3 min and check for agglomerates. Heat phase A/B and phase C separately to 75° C. Add phase C to phase A/B with stirring and homogenise for 2 min using the Ultra-Turrax T25 (yellow-green setting, 8000-9500 rpm). Add phase D at between 55 and 60° C., add phase E at 40° C., and cool to room temperature with further stirring; adjust the pH to 7.0 using 30% citric acid. Then transfer into suitable containers. A light, slightly opaque foundation is obtained which is suitable for all skin types. Avocado oil, vitamin E acetate and cell-protecting RonaCare ® ectoin support the skin-care action.
Sources of supply:
(1) Merck KGaA/Rona ®
(2) C.P. Kelco
(3) BASF AG
(4) Kronos International Inc.
(5) Les Colorants Wackherr
(6) Sasol Germany GmbH
(7) Cognis GmbH
(8) Seppic
(9) Gustav Heess GmbH
(10) Symrise
(11) Elementis Specialities
(12) Clariant GmbH

Example A5

Body Lotion

| Raw material | | INCI | [%] |
|---|---|---|---|
| Phase A | | | |
| Aloe vera gel 10x decolorised | (1) | ALOE BARBADENSIS | 2.00 |
| D-Panthenol | (2) | PANTHENOL | 0.40 |
| Pigment from Example 1 | | | 6.00 |
| RonaCare ® allantoin | (3) | ALLANTOIN | 0.20 |
| Glycerin, anhydrous | (3) | GLYCERIN | 4.00 |
| Water, demineralised | | AQUA (WATER) | 67.57 |
| Phase B | | | |
| Protelan AGL 95/C | (4) | SODIUM COCOYL GLUTAMATE | 6.00 |
| Cosmacol EMI | (5) | DI-C12-13 ALKYL MALATE | 3.00 |
| Eutanol G | (6) | Octyldodecanol | 3.00 |
| Jojoba oil | (7) | SIMMONDSIA CHINENSIS (JOJOBA OIL) | 1.50 |
| Tegosoft TN | (8) | C12-15 Alkyl Alkyl benzoate | 1.50 |
| Carbopol ETD 2020 | (9) | Acrylates/C10-30 Alkyl Acrylate Crosspolymer | 0.60 |
| Phenonip | (10) | Phenoxyethanol, Butylparaben, Ethylparaben, Propylparaben, Methylparaben | 0.60 |
| RonaCare ® bisabolol | (3) | Bisabolol | 0.50 |
| RonaCare ® all-rac-alpha-tocopheryl acetate | (3) | Tocopheryl Acetate | 0.50 |
| Oxynex ® ST liquid | (3) | Diethylhexyl Syringylidenemalonate, Caprylic/Capric Triglyceride | 0.50 |
| Cremophor RH 410 | (11) | PEG-40 Hydrogenated Castor Oil | 0.30 |
| Oxynex ® K liquid | | PEG-8, Tocopherol, Ascorbyl Palmitate, Ascorbic Acid, Citric Acid | 0.03 |
| Phase C | | | |
| Lifetime DH10255/1 perfume oil | (12) | Perfume | 0.50 |
| Phase D | | | |
| Water, demineralised | | Aqua (Water) | 1.00 |
| Germal 115 | (13) | Imidazolidinyl Urea | 0.30 |

Preparation: Pre-dissolve the aloe vera and RonaCare ® allantoin in the water of phase A with stirring, then add the other constituents of phase A and heat to 60° C. Introduce the jojoba oil, Oxynex K liquid, Cosmacol EMI, Eutanol G and Tegosoft TN into a stirred vessel, then incorporate the carbopol homogeneously using the disperser disc (about 700 rpm, 20 min). Then add the remaining constituents of phase B, and stir everything to give a homogeneous mixture, only adding the Protelan AGL 95/C right at the end of phase B in order to prevent excessive incorporation of air. Slowly emulsify phase A into phase B (RT) at 60° C. with the aid of the disperser disc. Add phases C and D, then homogenise for 4 min using the Ultra-Turrax T50, speed 4. Cool to room temperature.
pH (23° C.) = 5.5-6.0
Viscosity: Brookfield DV II + Helipath, spindle C, 5 rpm, 24° C. = 11200 mPa s Sources of supply:
(1) Terry Laboratoires
(2) Alfa Aesar GmbH & Co. KG
(3) Merck KGaA/Rona ®
(4) Zschimmer & Schwarz GmbH & Co.
(5) Nordmann, Rassmann GmbH & Co.
(6) Cognis GmbH
(7) Gustav Heess GmbH
(8) Evonik Goldschmidt GmbH
(9) Noveon
(10) Clariant GmbH
(11) BASF AG
(12) Parfex
(13) ISP Global Technologies Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure[s] of all applications, patents and publications, cited herein and of corresponding German application No. DE 102009051171.7, filed Oct. 29, 2010, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A pigment comprising spherical particles of magnesium silicate, aluminium silicate, alkali-metal aluminium silicates, alkaline-earth metal aluminium silicates or combinations thereof, having a particle diameter of 0.1-100 μm and coated on the surface with agglomerates of $ZrO_2$, $ZnO$, $Al_2O_3$, $TiO_2$, $Fe_2O_3$, $Fe_3O_4$, $FeOOH$, $BaSO_4$ or mixtures thereof thereby forming a 1st layer, and optionally coated with a further layer comprising a metal oxide or metal-oxide mixture, a lake or Berlin Blue thereby forming a 2nd layer.

2. The pigment according to claim 1, having an outer top layer comprising $SiO_2$.

3. The pigment according to claim 1, wherein the 1st layer has an average layer thickness of 0.01-2μm.

4. The pigments according to claim 2, wherein the outer top layer has an average thickness of 0.01-1μm.

5. The pigments according to claim 1, wherein the spherical particles have the following coating arrangement on the surface:
spherical particle+$TiO_2$
spherical particle+$TiO_2$ $_{+SiO2}$
spherical particle+$TiO_2$/$Fe_2O_3$
spherical particle+$TiO_2$/$Fe_2O_3$+$SiO_2$
spherical particle+$Fe_2O_3$+$SiO_2$
spherical particle+$FeO(OH)$+$SiO_2$
spherical particle+$Fe_3O_4$ +$SiO_2$
spherical particle+$TiFe_2O_5$+$SiO_2$
spherical particle+$TiO_2$+$Fe_2O_3$+$SiO_2$
spherical particle+$TiO_2$+$Fe_3O_4$+$SiO_2$
spherical particle+$TiO_2$+$Fe_4[Fe(CN)_6]_3$
spherical particle+$TiO_2$+$Fe_4[Fe(CN)_6]_3$+$SiO_2$
spherical particle+$TiO_2$+carmine lake or
spherical particle+$TiO_2$+carmine lake+$SiO_2$.

6. The pigment according to claim 1, having an oil absorption value determined in accordance with DIN ISO 787/5-1980 (E) of 10-200.

7. The pigment according to claim 1, having a BET surface area determined in accordance with DIN 9277:2003-05 of 1-200 m²/g.

8. The pigment according to claim 1, having an outer protective layer which is capable of increasing the light, temperature and/or weather stability of the pigments.

9. A process for preparing the pigment according to claim 1, comprising coating the spherical particles with the agglomerates by precipitation in aqueous suspension by substantially uniform and simultaneous or non-simultaneous addition of solutions of agglomerate- or layer-forming raw materials in the presence of an acid or base, followed by filtering off, washing, drying, and optionally calcining and sieving.

10. A product selected from the group consisting of paints, coatings, printing inks, security printing inks, plastics, ceramic materials, glasses, cosmetic formulations, tracers, fillers, pigment preparations and dry preparations, comprising pigments according to claim 1 and a carrier.

11. A composition comprising a pigment according to claim 1 and a carrier.

12. A composition according to claim 11, wherein the carrier is selected from the group consisting of absorbents, astringents, antimicrobial substances, antioxidants, antiperspirants, antifoaming agents, antidandruff active compounds, antistatics, binders, biological additives, bleaches, chelating agents, deodorisers, emollients, emulsifiers, emulsion stabilisers, dyes, humectants, film-formers, fillers, fragrances, flavours, insect repellents, preservatives, anticorrosion agents, cosmetic oils, solvents, oxidants, vegetable constituents, buffer substances, reducing agents, surfactants, propellant gases, opacifiers, UV filters, UV absorbers, denaturing agents, viscosity regulators, perfumes and vitamins.

13. A cosmetic composition comprising a pigment according to claim 1 and a cosmetically acceptable carrier.

14. A pigment according to claim 1, wherein the spherical particles have a particle diameter of 0.3-50 μm.

15. A pigment according to claim 1, wherein the spherical particles have a particle diameter of 0.5-15 μm.

16. A pigment according to claim 1, wherein the spherical partial mixtures are selected from a group consisting of
   A. alkali-metal aluminium silicates and magnesium silicate,
   B. alkali-metal aluminium silicates and silicon dioxide, and
   C. alkali-metal aluminium silicates and alkaline-earth metal aluminium silicates.

* * * * *

UNITED STATES PATENT AND TRADEMARK OFFICE
CERTIFICATE OF CORRECTION

PATENT NO. : 8,524,261 B2  
APPLICATION NO. : 12/911885  
DATED : September 3, 2013  
INVENTOR(S) : Christoph Schmidt et al.

It is certified that error appears in the above-identified patent and that said Letters Patent is hereby corrected as shown below:

IN THE CLAIMS:

Column 16, line 41, (Claim 5), reads: -- spherical particle + $TiO_{2 + SiO2}$ --.

Should read: -- spherical particle + $TiO_2$ + $SiO_2$ --.

Signed and Sealed this
Twenty-eighth Day of January, 2014

Michelle K. Lee
*Deputy Director of the United States Patent and Trademark Office*